(12) United States Patent
Shin et al.

(10) Patent No.: US 9,322,824 B2
(45) Date of Patent: Apr. 26, 2016

(54) IMMUNOCHROMATOGRAPHY DETECTION SENSOR COMPRISING OPTICAL WAVEGUIDE AND A DETECTION METHOD USING THE SAME

(71) Applicants: Korea Research Institute of Bioscience and Biotechnology, Daejeon (KR); Infopia Co., Ltd, Gyeonggi-Do (KR)

(72) Inventors: Yong Beom Shin, Daejeon (KR); Min Gon Kim, Daejeon (KR); Byeong Woo Bae, Anyang-si (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 236 days.

(21) Appl. No.: 14/222,291

(22) Filed: Mar. 21, 2014

(65) Prior Publication Data

US 2014/0206103 A1 Jul. 24, 2014

Related U.S. Application Data

(63) Continuation of application No. 13/054,168, filed as application No. PCT/KR2009/003960 on Jul. 17, 2009, now abandoned.

(30) Foreign Application Priority Data

Jul. 18, 2008 (KR) ........................ 10-2008-0070196

(51) Int. Cl.
| | |
|---|---|
| *G01N 21/00* | (2006.01) |
| *G01N 33/543* | (2006.01) |
| *G01N 21/77* | (2006.01) |
| *G01N 33/558* | (2006.01) |
| *G01N 30/95* | (2006.01) |

(52) U.S. Cl.
CPC ...... *G01N 33/54373* (2013.01); *G01N 21/7703* (2013.01); *G01N 33/558* (2013.01); *G01N 30/95* (2013.01); *G01N 2021/7766* (2013.01)

(58) Field of Classification Search
CPC .......... C12Q 1/6834; C12Q 2563/103; C12Q 1/6816; C12Q 2563/137; C12Q 1/6818; C12Q 2565/501; C12Q 2563/107; C12Q 1/6837; G01N 33/585; G01N 15/14; G01N 15/1459; G01N 33/54373; G01N 21/7703
See application file for complete search history.

(56) References Cited

U.S. PATENT DOCUMENTS

| | | | | |
|---|---|---|---|---|
| 5,376,556 A | * | 12/1994 | Tarcha | ................. G01N 21/658 |
| | | | | 435/968 |
| 5,604,105 A | * | 2/1997 | Jackowski | ......... C07K 16/4283 |
| | | | | 422/430 |

OTHER PUBLICATIONS

Sajid et al. "Designs, formats and applications of lateral flow assay: A literature review", J. Saudi Chem. Soc., 2015, v. 19, pp. 689-705.*

*Primary Examiner* — Yelena G Gakh
(74) *Attorney, Agent, or Firm* — Sterne, Kessler, Goldstein & Fox P.L.L.C.

(57) ABSTRACT

The present invention relates to an immunochromatographic detection sensor comprising optical waveguides and a detection method using the same, and more particularly, to an immunochromatographic detection sensor comprising optical waveguides, in which the optical waveguides are provided under the membrane, probe beams transmitted through the optical waveguide maximize the interaction frequency between evanescent wave generated on the surface of the optical waveguide and the colored conjugate in the band formed on the membrane, resulting in the absorbance signal from the colored conjugate being greatly amplified to improve the sample detection sensitivity, and to a detection method using the same.

20 Claims, 6 Drawing Sheets

IMMUNOCHROMATOGRAPHY DETECTION SENSOR COMPRISING OPTICAL WAVEGUIDE AND A DETECTION METHOD USING THE SAME

CROSS-REFERENCE TO RELATED APPLICATIONS

This application is a continuation of U.S. application Ser. No. 13/054,168, which is a 371 of International Application PCT/KR2009/003960 filed on Jul. 17, 2009, the disclosures of which are incorporated by reference herein in their entireties.

BACKGROUND OF THE INVENTION

1. Technical field

The present invention relates to an immunochromatographic detection sensor comprising optical waveguides and a detection method using the same, and more particularly, to an immunochromatographic detection sensor comprising optical waveguides, in which the optical waveguides are provided under the membrane, probe beams transmitted through the optical waveguide maximize the interaction frequency between evanescent waves generated on the surface of the optical waveguide and the colored conjugates in the colored conjugate bands formed on the membrane, resulting in an absorbance signal from the colored conjugate that is greatly amplified to improve the sample detection sensitivity, and a detection method using the same.

2. Background Art

In a lateral flow membrane-based immunochromatographic assay, a liquid sample is absorbed and migrates by capillary action through an antibody-coated membrane, in which a conjugate pad is in contact with a sample pad on the top of the membrane and an absorbent pad is placed on the end of the membrane. A colored conjugate, on which a substance capable of selectively binding with the sample material is immobilized, is dried on the conjugate pad. On the membrane, a substance capable of selectively capturing the sample material and a substance capable of binding the substance that is immobilized on the colored conjugate are immobilized at different positions, such as sample lines or control lines. The substances immobilized on the membrane and the colored conjugate, which selectively bind to the sample material, are constructed to bind with the sample material in a sandwich-type structure. The absorbent pad is made of a strongly liquid-absorbing material. Upon applying a liquid sample to the immunochromatographic analysis device, if the analyte is present in the liquid sample, the substance specific to the analyte and the substance specific to the substance immobilized onto the colored conjugate form colored bands on each position of the membrane. The results are qualitatively read with the naked eye or quantitatively analyzed with the help of a digital sensor. When the colored bands are analyzed with the naked eye or with the help of a digital sensor, light reflected perpendicularly to the membrane surface is measured to analyze the colored conjugate bands.

However, the known measurement methods have low sensitivity (detection limit: approximately 1 ng/mL of antigen protein), and thus it is difficult to employ the methods for high sensitivity detection.

BRIEF SUMMARY OF THE INVENTION

Technical Problem

Accordingly, the present inventors have made many efforts to solve the above problem that is generated upon reading the diffuse light reflected from the membrane surface. As a result, they have successfully developed an immunochromatographic detection sensor comprising optical waveguides and a detection method using the same. They found that when the optical waveguides are provided under the membrane, probe beams transmitted through the optical waveguide maximize the interaction frequency between evanescent waves generated on the surface of the optical waveguide and the colored conjugate in the colored conjugate bands formed on the membrane, and thus the absorbance signal from the colored conjugate is greatly amplified to improve the sample detection sensitivity, thereby completing the present invention.

Technical Solution

It is an object of the present invention to provide an immunochromatographic detection sensor comprising optical waveguides, in which the optical waveguides are provided under the membrane, probe beams transmitted through the optical waveguide maximize the interaction frequency between evanescent wave generated on the surface of optical waveguide and the colored conjugate in the colored conjugate bands formed on the membrane, and thus the absorbance signal from the colored conjugate is greatly amplified to improve the sample detection sensitivity.

It is another object of the present invention to provide an immunochromatographic detection method using the immunochromatographic detection sensor comprising optical waveguides.

Advantageous Effects

According to the immunochromatographic detection sensor comprising optical waveguides and the detection method using the same of the present invention, the optical waveguides are provided under the membrane and probe beams transmitted through the optical waveguide maximize the interaction frequency between evanescent waves generated on the surface of optical waveguide and the colored conjugate in the colored conjugate bands formed on the membrane, and thus the absorbance signal from the colored conjugate is greatly amplified, thereby improving the sample detection sensitivity.

BRIEF DESCRIPTION OF THE DRAWINGS/FIGURES

Figure 5:
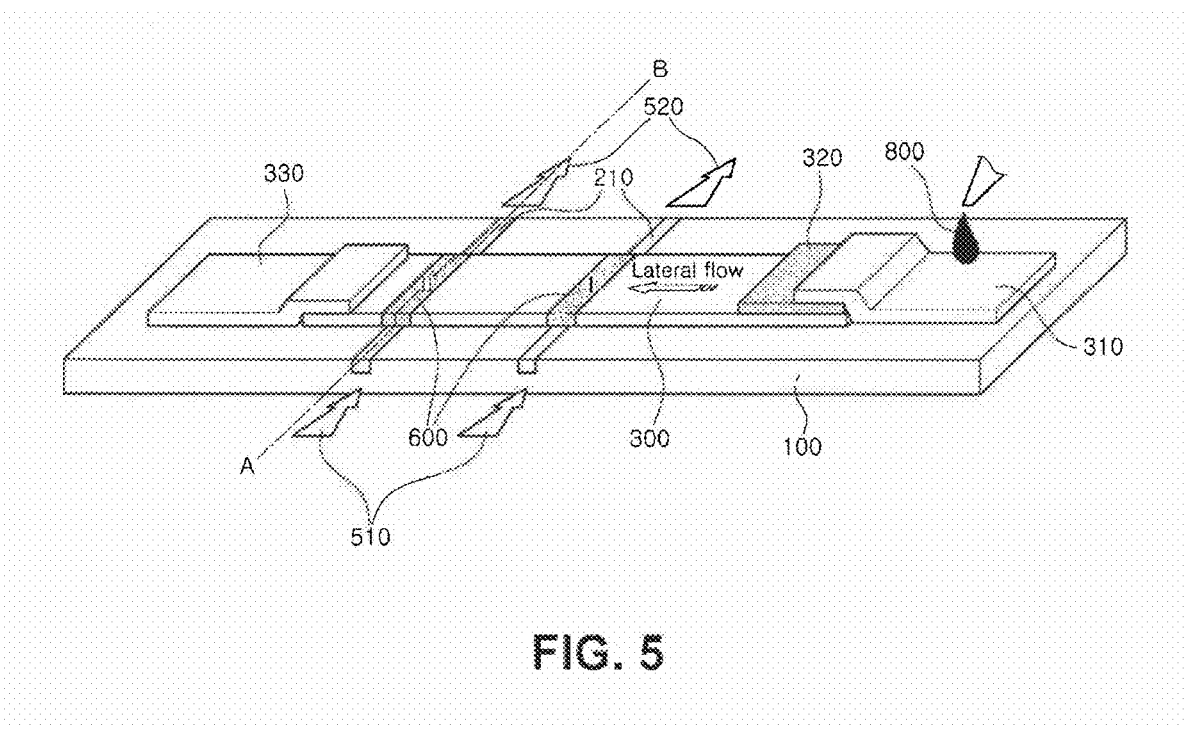
Figure 6:
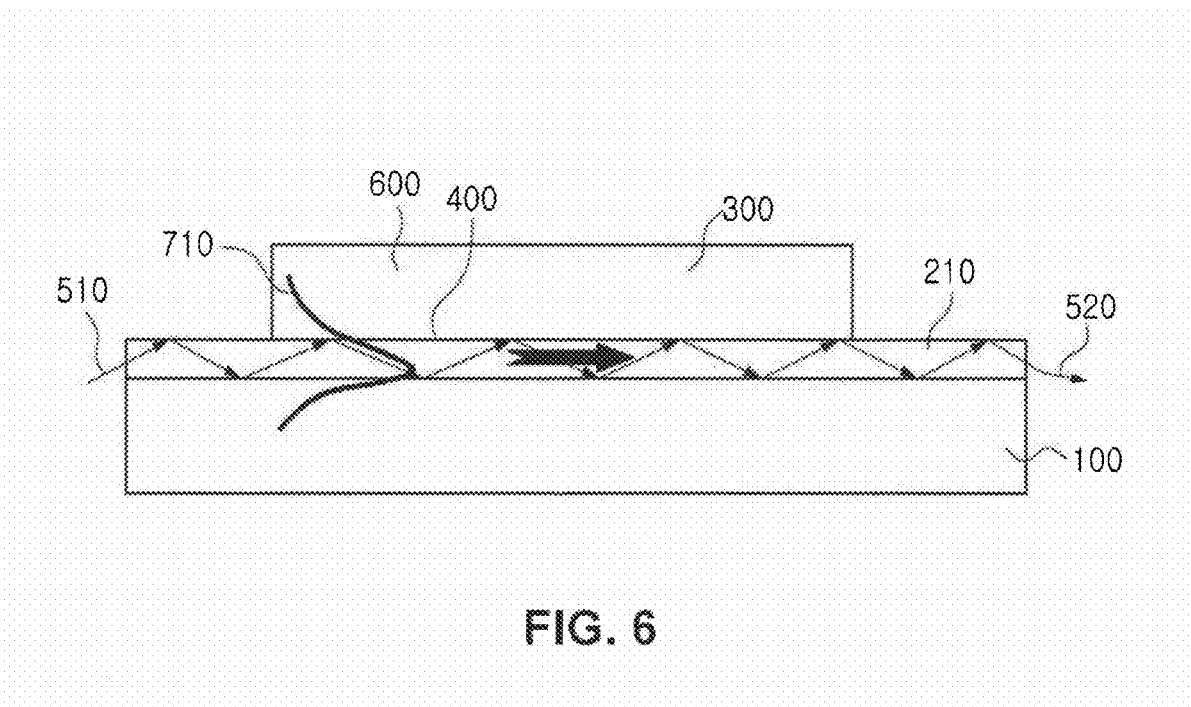

FIG. 5 is a schematic diagram showing the sample migration direction, colored conjugate bands formation, and input probe beam, when the sample is analyzed using the immunochromatographic detection sensor provided with the channel optical waveguides according to the present invention; and FIG. 6 is a cross-sectional view of channel optical waveguide membrane sensor, taken along the line A-B of FIG. 5.
100: Substrate
200: Optical waveguide
210: Channel optical waveguide
300: Membrane
310: Sample pad
320: Conjugate pad
330: Absorbent pad
400: Interface
500: Probe beam
510: Input probe beam
520: Output probe beam
600: Colored conjugate band
700: Evanescent wave of probe beam
800: Sample
I: Sample line
II: Control line

DETAILED DESCRIPTION OF THE INVENTION

Best Mode

In order to achieve the above objects, in accordance with one aspect, the present invention provides a lateral flow membrane-based immunochromatographic detection sensor, comprising (a) conjugate pad containing a first receptor and a light-absorbing metal particle; (b) a membrane containing a sample line region and control line region; (c) a substrate provided under the membrane; and (d) two optical waveguides. More particularly, the present invention provides a lateral flow membrane-based immunochromatographic detection sensor, comprising (a) a conjugate pad containing (i) a first receptor capable of binding specifically to an analyte in a sample; and (ii) a light-absorbing metal particle capable of binding to the first receptor or bound to the first receptor, wherein the light-absorbing metal particle binds with the first receptor before or during the sample migration, thereby forming a colored conjugate, and the colored conjugate moves together with the sample during the sample migration along the following membrane;

(b) a membrane containing (i) a sample line region having a second receptor capable of binding specifically to the analyte, wherein the second receptor immobilized to the sample line region captures the analyte bound to the first receptor of the colored conjugate, thereby forming a first colored conjugate band; and (ii) a control line region having a third receptor capable of binding specifically to the first receptor, wherein the third receptor immobilized to the control line region captures the first receptor of the colored conjugate which is not bound to the analyte, thereby forming a second colored conjugate band;

(c) a substrate provided under the membrane; and (d) two optical waveguides for transmitting the light as a probe beam, while being positioned between the membrane and the substrate, wherein each optical waveguide is entirely overlapped with the sample line region or the control line region, wherein an energy of the evanescent wave is generated from the probe beam, at the interface between the membrane and the optical waveguide, and the colored conjugate band absorbs the energy of the evanescent wave, thereby reducing the amount of the energy of the evanescent wave and reducing the intensity of the output probe beam, depending on the amount of the colored conjugates present in the colored conjugate band.

In the present invention, the immunochromatographic detection sensor is characterized in that the colored conjugate band, which absorb the energy of the evanescent wave that is generated at the interface between the membrane and the optical waveguide is formed on the membrane, while the probe beam is transmitted through the optical waveguide.

In the present invention, the immunochromatographic detection sensor is characterized in that the amount of the colored conjugate present in the colored conjugate band is determined by the intensity of the output probe beam, so as to analyze the component of analyte in the sample.

The principle of the present invention is based on optical waveguide theory.

Figure 1:
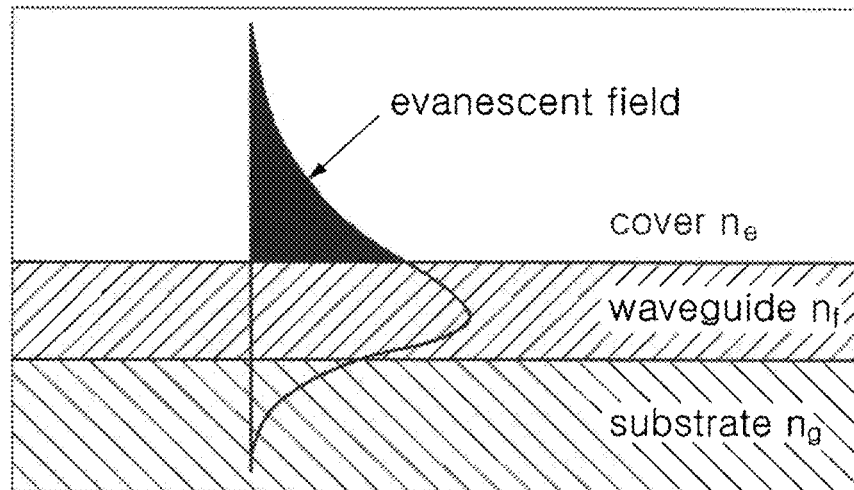
FIG. 1 is a diagram showing electromagnetic field of evanescent wave, generated by probe beams that are transmitted through the optical waveguide on the substrate.
Figure 2:
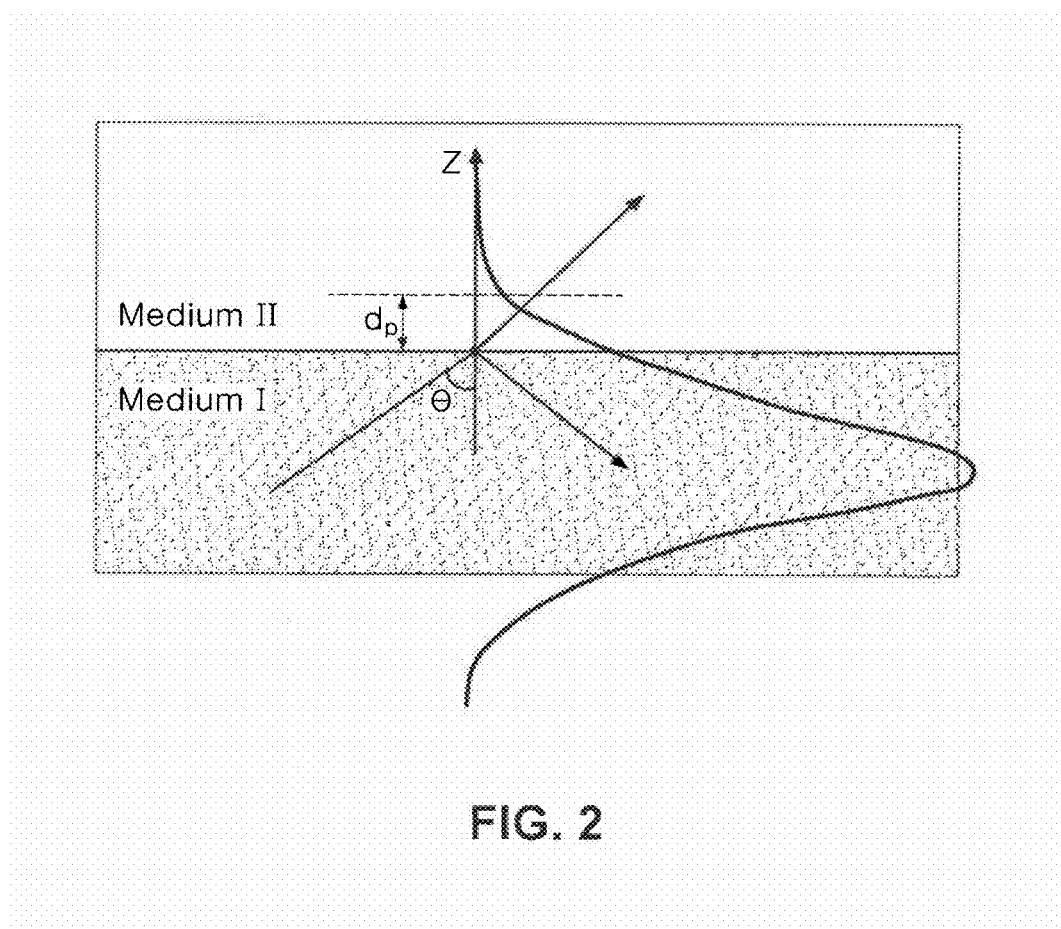
FIG. 2 is a diagram showing evanescent wave and penetration depth, when total internal reflection occurs at the interface between the optical waveguide and the upper layer.

The electromagnetic field intensity of the light beam that is transmitted through a film-type optical waveguide formed on a substrate shows a Gaussian distribution around the waveguide. However, in a general optical waveguide sensor, the substrate has a higher refractive index than the upper medium, showing asymmetric distribution as in FIG. 1. In this connection, the electromagnetic field amplitude decreases exponentially with the distance from the interfaces of the lower substrate and the upper medium II. The detailed description will be made with reference to FIG. 2.

When light from the medium I (optical waveguide) with a refractive index $n_i$ is transmitted to another medium II with a refractive index $n_2$, reflection or refraction occurs at the interface. If the refractive index is $n_2 < n_1$, total internal reflection occurs at an incident angle equal to, or greater than the critical angle ($\theta_c$). In this connection, the critical angle ($\theta_c$) is expressed by the following Equation 1.

$$\theta = \sin^{-1}(n_2/n_1) \qquad \text{[Equation 1]}$$

If total internal reflection occurs, not all light is reflected at the interface, but there is some penetration into the second medium. More specifically, the electromagnetic field amplitude does not rapidly come to zero at the interface, and but rather has the function of decreasing exponentially with the distance from the interface. Therefore, it is called an evanescent wave, and the light intensity at the interface is expressed by the following Equation 2.

$$E = E_0 e^{-(z/d_p)} \qquad \text{[Equation 2]}$$

wherein $d_p$ is defined as the distance from the interface where the light intensity decays to 1/e of its original value, and z is in a direction perpendicular to the interface of two mediums.

The depth of penetration, $d_p$ is determined by the following Equation 3.

$$\frac{\lambda}{d_p} = 2\pi n_1 \sqrt{\sin^2\theta - \left(\frac{n_2}{n_1}\right)^2} \qquad \text{[Equation 3]}$$

wherein $\lambda$ and $\theta$ represent wavelength and angle of incidence, respectively.

Figure 3:
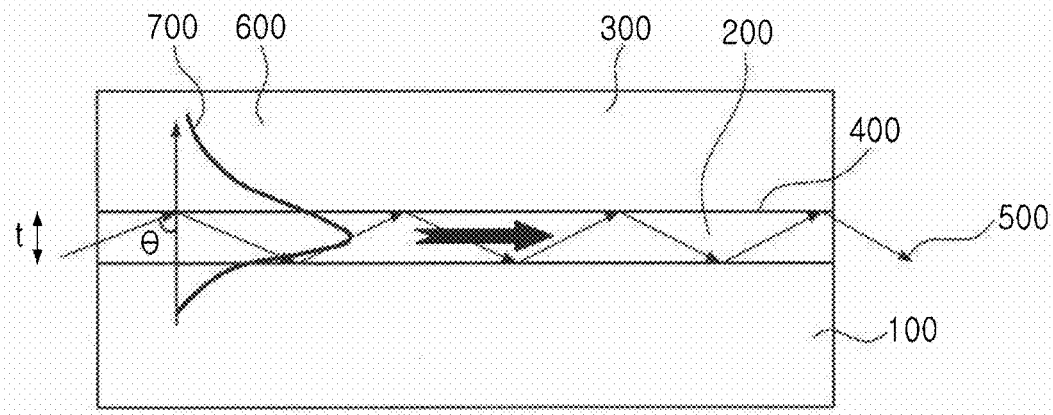
FIG. 3 is a diagram showing multiple total internal reflection at the interface of the upper solid membrane, when the probe beam is transmitted through the optical waveguide on the substrate.

As proposed by the present invention, FIG. 3 is a diagram showing a membrane optical waveguide sensor, consisting of an optical waveguide 200 that is fabricated on a substrate 100 and a membrane 300 that is disposed on the optical waveguide 200. From the viewpoint of the geometrical optics, the number (N) of total internal reflection, which occurs at the interface 400 between the optical waveguide and the upper medium, membrane 300 while passing through the optical waveguide 200, can be defined by the following Equation 4.

$$N = \frac{L}{(2t)\tan\theta} \quad \text{[Equation 4]}$$

wherein L and t represent the length and thickness of the optical waveguide, respectively.

For example, if the optical waveguide 200 has a length of 5 mm, a thickness of 1 μm, and an angle of incidence of 40°, the number of total internal reflection that occurs at the interface 400 between the optical waveguide 200 and the membrane 300 is close to 3000. If the colored conjugate band 600 is formed in the solid membrane 300, the probe beam 500 is transmitted through the optical waveguide, and total internal reflection occurs 3000 times at the interface 400, and the evanescent wave 700 of the probe beam 500 is absorbed by the colored conjugate present in the colored conjugate band 600. Consequently, the intensity of output probe beam 500 from the optical waveguide 200 weakens. Thus, the amount of the colored conjugate can be determined by measuring the intensity.

In the present invention, the two colored conjugate band may be formed on the membrane. The first colored conjugate band may be formed by the binding of a second receptor and an analyte, and the second colored conjugate band may be formed by the binding of a third receptor and a first receptor.

The three receptors are present in the lateral flow membrane-based immunochromatographic detection sensor in the present invention.

The first receptor is positioned in the conjugate pad and can bind specifically to the analyte for detection in a sample. The light-absorbing metal particle can bind to the first receptor, and a colored conjugate is formed by binding the first receptor and the light-absorbing metal particle. Then, the formed colored conjugate moves together with the sample along the membrane in the present invention.

The second receptor is immobilized to the sample line region and the third receptor is immobilized to the control line region. The second receptor can bind specifically to the analyte in common with the first receptor, and can bind to the analyte simultaneously with the first receptor. The first colored conjugate band is formed by binding the second receptor and analyte bound to the first receptor of the colored conjugate in the sample line region. The third receptor can bind specifically to the first receptor of the colored conjugate which is not bound to the analyte, and the second colored conjugate band is formed by binding the first receptor and the third receptor in the control line region.

In the present invention, the membrane contains the sample line region (I of FIGS. 4 and 5) and control line region (II of FIGS. 4 and 5), and may be made of one or more selected from the group consisting of nitrocellulose, glass fiber, polyethylene, polycarbonate, and polystyrene, but is not limited thereto.

In the present invention, the membrane typically has a thickness in the range of 1~100 μm.

The substrate according to the present invention should be transparent to the probe beam, and its refractive index is lower than that of the optical waveguide.

In the present invention, the substrate 100 is provided under the membrane 300, and may be typically made of any one selected from glass; quartz; alumina ($Al_2O_3$); plastic such as PMMA (polymethylmethacrylate), PS (polystyrene), and COC (cyclic olefin copolymer); and silicone.

If the substrate is a silicon substrate that is generally used for electronic applications, the substrate is coated with a dielectric thin film such as $SiO_2$, which is transparent to visible light and has a low refractive index, so that it has a thickness in the range of 300~1000 nm as an underlayer, and then the optical waveguide is provided thereon.

The optical waveguide according to the present invention should be transparent to the probe beam and have a higher refractive index than the substrate or the underlayer. Typically, the optical waveguide consists of a thin dielectric film, fabricated by using dielectric materials with a high refractive index such as $Al_2O_3$ $Si_3N_4$ $TiO_2$ plastic such as PMMA (polymethylmethacrylate), PS (polystyrene), and COC (cyclic olefin copolymer). The dielectric thin-film optical waveguide may be generally fabricated by any thin film fabrication method selected from Chemical Vapor Deposition (CVD), sputtering, evaporation (thermal evaporation and E-beam evaporation), and spin coating methods.

Two optical waveguides for transmitting the light as a probe beam may be present in the lateral flow membrane-based immunochromatographic detection sensor in the present invention. In this case, optical waveguides are positioned between the membrane and the substrate, and each optical waveguide is entirely overlapped with the sample line region or the control line region.

That is, the present invention is characterized in that the entire or a portion of the optical waveguides, through which the probe beam passes, is overlapped with the colored conjugate bands formed on the sample line region and the control line region.

In the present invention, the optical waveguide may be selected from the group consisting of a slab waveguide, a channel waveguide, and a rib waveguide.

In one embodiment of the present invention, an immunochromatographic detection sensor comprising channel optical waveguides was fabricated.

In the present invention, the channel or rib optical waveguides may be arranged in parallel with each other, and each of them is overlapped with each lower portion of the sample line region and control line region, so that an independent light source can be used for each optical waveguide.

In the present invention, the channel or rib optical waveguides may have a Y-shaped structure, in which the optical waveguides have one probe beam input port, and the branched optical waveguides are overlapped with each lower portion of the sample line region and control line region, so that one light source can be used for the optical waveguides.

In the present invention, the optical waveguide typically has a thickness and width in the range of 300 nm~1000 μm.

In the present invention, the wavelength of the probe beam may be selected from the group consisting of ultraviolet, visible, and infrared rays.

In the present invention, the light source for the probe beam may be selected from the group consisting of laser, LED and halogen lamp.

In the present invention, the coupling method for transmitting the probe beam through the optical waveguide may be performed by using one selected from the group consisting of object lens, prism and diffraction grating.

In the present invention, the probe beam is transmitted through the optical waveguide overlapped with the lower portion of the sample line and control line regions of the membrane, and thereafter the output probe beam from the optical waveguide is measured using a detector selected from the group consisting of photodiode (PD), photo-multiplier tube (PMT), CCD (charge coupled device), and CMOS (complementary metal oxide semiconductor).

In the present invention, the amount of the colored conjugate is determined by the evanescent wave absorption, in which the intensity of the output probe beam may be determined by measuring any one selected from the group consisting of probe beam intensity at a single wavelength, white light intensity, change in probe beam wavelength, and change in probe beam phase.

In the present invention, the colored conjugate may be formed by binding the light-absorbing metal particle and the first receptor before or during the sample migration. The colored conjugate may be characterized in that the first receptor capable of binding specifically to the analyte in the sample is conjugated to the surface of the light-absorbing metal particle.

In the present invention, the light-absorbing metal particle may comprise all metal particles capable of absorbing the light according to the purpose of the present invention, and may be made of materials selected from the group consisting of metals such as gold and silver, magnetic substances such as Fe, Co, Ni, and rare earth elements (neodymium (Nd), gadolinium (Gd) etc.), but not limited to.

In the present invention, the light-absorbing metal particle may be a nanoparticle, and the nanoparticle may have a size in the range of 5~200 nm.

In the present invention, the receptors comprising the first receptor, second receptor and third receptor may be proteins, DNAs, peptides, amino acids, aptamers, or combinations thereof.

In accordance with another aspect, the present invention provides an immunochromatographic detection method, comprising the steps of: 1) applying a sample to the membrane of the lateral flow membrane-based immunochromatographic detection sensor in the present invention, 2) moving the sample along the membrane, 3) transmitting the probe beam through the optical waveguide, and 4) determining the intensity of the colored conjugate band by the intensity of the output probe beam, so as to analyze the component of analyte in the sample.

According to the immunochromatographic detection method of the present invention, probe beam transmitted through the optical waveguide maximizes the interaction frequency between evanescent wave generated on the surface of optical waveguide and the colored conjugates present in the colored conjugate band formed on the membrane, and thus the absorbance signal from the colored conjugate is greatly amplified to improve the sample detection sensitivity.

These and other objects, features, and advantages of the present invention will become more apparent from the following detailed description of the preferred embodiment with reference to the accompanying drawings. Hereinafter, the immunochromatographic detection sensor provided with optical waveguides according to the preferred Example of the present invention will be described in detail with reference to the accompanying drawings.

In accordance with one embodiment, proposed by the present invention, a specific detection sensor provided with a channel optical waveguide and an immunochromatography membrane will be described with reference to FIG. 4.

A channel optical waveguide 210 is provided on a glass substrate 100. The channel optical waveguide can be fabricated by the general thin film fabrication method and patterning method. If necessary, a K$^+$ ion exchange process is performed. The exchange of K$^+$ for Na$^+$ ions in the glass substrate produces a channel in the exposed portion of higher refractive index than the remainder of the substrate, thus, defining a waveguide.

A nitrocellulose membrane 300 is provided on the substrate 100 having the channel optical waveguide 210 formed thereon. In this connection, it is important that the membrane is optically coupled to the optical waveguide 210.

A conjugate pad 320, where the dried colored conjugate capable of selectively binding with an analyte in the sample is contained, is placed at one end of the membrane, and a sample pad 310 capable of holding the liquid sample dropped therein for a predetermined time is provided on the upper portion of the conjugate pad.

The colored conjugate consists of the first receptor capable of selectively binding with the sample material, immobilized on the surface of any one selected from metal nanoparticles, colored polymer particles, and silica particles. The first receptor is selected from antibodies, DNAs, peptides, aptamers, and amino acids that selectively bind with the analyte in the sample. The particle has a size of 5~200 nm.

An absorbent pad 330 is placed at the other end of the membrane, in which the absorbent pad is made of a strongly liquid-absorbing material. The second receptor (e.g.,capture antibody) specific to the analyte in the sample and the third receptor (e.g., secondary antibody) specific to the first receptor (e.g., detection antibody) immobilized on the colored conjugate are previously immobilized on (I) region (sample line region) and (II) region (control line region) of the membrane, where each channel optical waveguide is positioned, respectively.

Meanwhile, FIG. 5 is a schematic diagram showing the sample migration direction, colored conjugate band formation, and input probe beam, when the sample is analyzed using the immunochromatographic detection sensor provided with the channel optical waveguides according to the present invention.

As shown in FIG. 5, when the sample 800 such as blood is applied onto the sample pad 310, the sample absorbed by the sample pad migrates to the conjugate pad 320, and binds with the dried colored conjugate in the conjugate pad, more exactly, with the analyte-specific first receptor immobilized on the surface of the colored conjugate.

As the sample continuously migrates along the membrane, the large-sized, insoluble solids present in the sample are filtered out by the membrane, and the sample moves by capillary action due to small-sized pores in the membrane, so as to reach the absorbent pad.

During the sample migration, the colored conjugate-analyte in the sample is captured by the analyte-specific second receptor that is previously immobilized at the region I, so as to form a first colored conjugate band. During the sample migration, the unbound colored conjugate continuously migrates, and is captured by the third receptor being specific to the first receptor, which is previously immobilized at the region II, so as to form a second colored conjugate band at the region II. The region I is a sample line that represents the concentration of the analyte in the sample, and the region II is a control line, indicating that the immunochromatographic assay is normally terminated.

When the sample migration and colored conjugate band formation are terminated, the probe beam 510 is introduced into each channel optical waveguide 210, and is transmitted through the channel optical waveguide. The probe beam is typically focused at the end of the channel optical waveguide using an objective lens or by other general methods.

FIG. 6 is a cross-sectional view of channel optical waveguide sensor, taken along the line A-B of FIG. 5.

As shown in FIG. 6, while the input probe beam 510 is transmitted through the optical waveguide, total internal reflection occurs several times at the interface 400, and the evanescent wave 710 of the input probe beam is absorbed by the colored conjugate 600, and thus the intensity of the output probe beam 520 from the channel optical waveguide 210 weakens. Thus, the amount of the colored conjugates present in the colored conjugate band can be determined by measuring the intensity.

The amount of the formed colored conjugates present in the colored conjugate band is proportional to the amount of analyte in the sample, suggesting that the intensity of the probe beam 520 is in inverse proportion to the amount of analyte in the sample.

Mode for Invention

Hereinafter, the constitution and effects of the present invention will be described in more detail with reference to Example. These examples are provided only for illustrating the present invention and should not be construed as limiting the scope and spirit of the present invention.

EXAMPLE 1

Immunochromatographic Detection Sensor Provided with Channel Optical Waveguides

Figure 4:
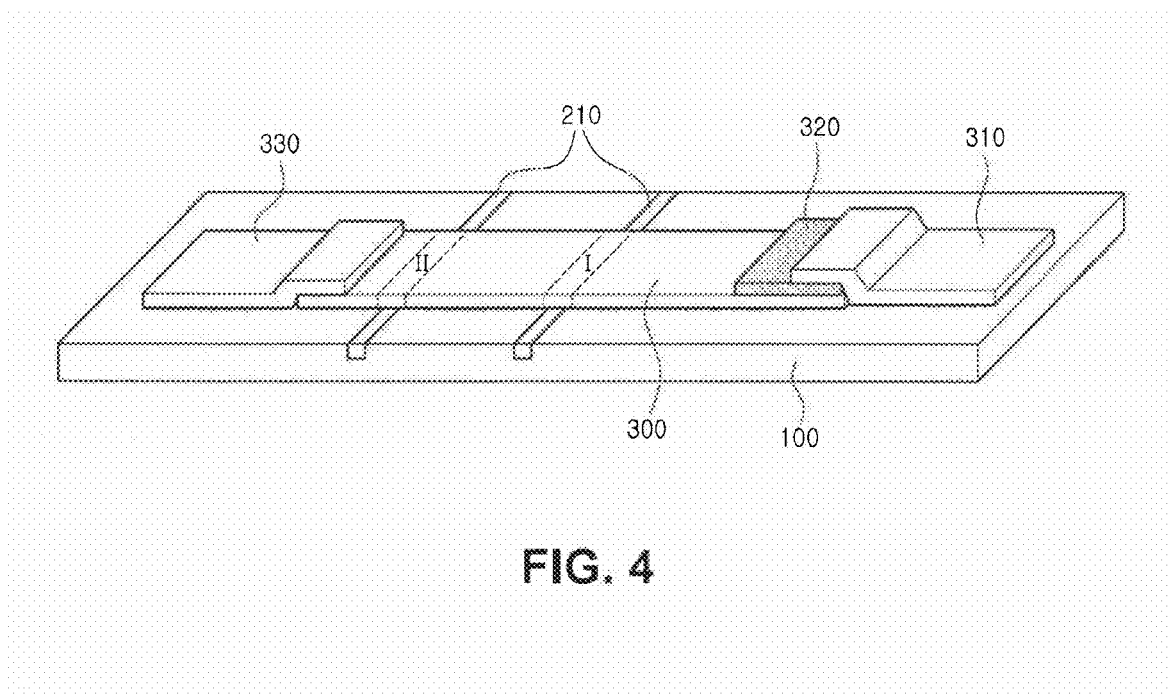
FIG. 4 is a diagram showing the immunochromatographic membrane connected with the channel optical waveguides according to the present invention.

As shown in FIG. 4, an immunochromatographic detection sensor provided with channel optical waveguides was fabricated.

The channel optical waveguides 210 were provided on the glass substrate 100.

The channel optical waveguides were fabricated by Chemical Vapor Deposition (CVD) and lithography.

The nitrocellulose membrane 300 was provided on the substrate 100 having the channel optical waveguide 210 formed thereon. In this connection, the membrane was optically coupled to the optical waveguide 210.

The conjugate pad, where the dried colored conjugate capable of selectively binding with an analyte in the sample was contained, was placed at one end of the membrane, and the sample pad 310 capable of holding the liquid sample dropped therein for a predetermined time was provided on the upper portion of the conjugate pad.

The colored conjugate was a detection antibody capable of selectively binding with the sample material, immobilized on the surface of gold nanoparticles with a size of 20 nm.

An absorbent pad 330 was placed at the other end of the membrane. The absorbent pad was made of a strongly liquid-absorbing material, glass fiber.

The second receptor (e.g., capture antibody) specific to the analyte in the sample and a third receptor (e.g., secondary antibody) specific to the first receptor (e.g., detection antibody) immobilized on the colored conjugate were previously immobilized on (I) and (II) regions of the membrane, where each channel optical waveguide was positioned, respectively.

When the sample 800 was applied onto the sample pad 310 of the immunochromatographic detection sensor that was provided with the channel optical waveguides according to the present invention, the sample absorbed by the sample pad migrated to the conjugate pad 320, and bound with the dried colored conjugate in the conjugate pad, and more specifically, with the analyte-specific first receptor immobilized on the surface of the colored conjugate. The sample continuously moved along the membrane to reach the absorbent pad.

During the sample migration, the colored conjugate-analyte in the sample was captured by the analyte-specific second receptor that was previously immobilized at the region I, so as to form a first colored conjugate band. During the sample migration, the unbound colored conjugate continuously migrated, and captured by the third receptor being specific to the first receptor, which was previously immobilized at the region II, so as to form a second colored conjugate band at the region II.

When the sample migration and colored conjugate band formation were terminated, the probe beam 510 was introduced into each channel optical waveguide 210, and was transmitted through the channel optical waveguide. The probe beam was typically focused at the end of the channel optical waveguide using an objective lens.

The present invention has been described in sufficient detail with a certain degree of specificity. It is understood to those skilled in the art that the present disclosure of embodiments has been made only by way of examples without departing from the spirit and scope of the invention as claimed. Accordingly, it is intended that the scope of the present invention be defined by the appended claims and equivalents thereof.

INDUSTRIAL APPLICABILITY

As described above, the present invention is to provide an immunochromatographic detection sensor comprising optical waveguides, in which the optical waveguides are provided under the membrane and probe beams transmitted through the optical waveguide maximize the interaction frequency between evanescent waves generated on the surface of the optical waveguide and the colored conjugate present in the colored conjugate band formed on the membrane, and thus the absorbance signal from the colored conjugate is greatly amplified to improve the sample detection sensitivity, and to a detection method using the same. The present invention is, therefore, very useful in the biosensor industry.

What is claimed is:

1. A lateral flow membrane-based immunochromatographic detection sensor, comprising
    (a) a conjugate pad containing (i) a first receptor capable of binding specifically to an analyte in a sample; and (ii) a light-absorbing metal particle capable of binding to the first receptor or bound to the first receptor,
        wherein the light-absorbing metal particle binds with the first receptor before or during the sample migration, thereby forming a colored conjugate, and the colored conjugate moves together with the sample during the sample migration along the following membrane;
    (b) a membrane containing
        (i) a sample line region having a second receptor capable of binding specifically to the analyte,
        wherein the second receptor immobilized to the sample line region captures the analyte bound to the first receptor of the colored conjugate, thereby forming a first colored conjugate band; and
        (ii) a control line region having a third receptor capable of binding specifically to the first receptor,
        wherein the third receptor immobilized to the control line region captures the first receptor of the colored conjugate which is not bound to the analyte, thereby forming a second colored conjugate band;
    (c) a substrate provided under the membrane; and
    (d) two optical waveguides for transmitting the light as a probe beam, while being positioned between the membrane and the substrate, wherein each optical waveguide is entirely overlapped with the sample line region or the control line region,
        wherein energy from the evanescent wave is generated by the probe beam, at the interface between the membrane and the optical waveguide, and the colored conjugate band absorbs the energy of the evanescent wave, thereby reducing the amount of the energy of the evanescent wave and reducing the intensity of the output probe beam, depending on the amount of the colored conjugates present in the colored conjugate band.

2. The immunochromatographic detection sensor according to claim 1, wherein the intensity of the colored conjugate bands is determined by the intensity of the output probe beam, so as to analyze the analyte in the sample.

3. The immunochromatographic detection sensor according to claim 1, wherein the membrane is made of one or more selected from the group consisting of nitrocellulose, glass fiber, polyethylene, polycarbonate, and polystyrene.

4. The immunochromatographic detection sensor according to claim 1, wherein the membrane has a thickness in the range of 1~100 μm.

5. The immunochromatographic detection sensor according to claim 1, wherein the substrate is made of any one selected from glass, quartz, alumina ($Al_2O_3$), PMMA (polymethylmethacrylate), PS (polystyrene), COC (cyclic olefin copolymer), and silicone.

6. The immunochromatographic detection sensor according to claim 5, wherein the substrate is coated with a $SiO_2$ thin film having a thickness in the range of 300~1000 nm as an underlayer, if the substrate is a silicon substrate.

7. The immunochromatographic detection sensor according to claim 1, wherein the optical waveguide is made of one material selected from the group consisting of $Al_2O_3$, $Si_3N_4$, $TiO_2$, PMMA (polymethylmethacrylate), PS (polystyrene), and COC (cyclic olefin copolymer).

8. The immunochromatographic detection sensor according to claim 1, wherein the optical waveguides are selected from the group consisting of slab waveguides, channel waveguides, and rib waveguides.

9. The immunochromatographic detection sensor according to claim 8, wherein the channel optical waveguides are arranged in parallel with each other.

10. The immunochromatographic detection sensor according to claim 1, wherein the optical waveguides have a thickness and width in the range of 300 nm~1000 μm.

11. The immunochromatographic detection sensor according to claim 1, wherein the light-absorbing metal particle is a nanoparticle.

12. The immunochromatographic detection sensor according to claim 11, wherein the nanoparticle has a size in the range of 5~200 nm.

13. The immunochromatographic detection sensor according to claim 1, wherein the receptors are protein, DNA, peptide, amino acid, aptamer, or combinations thereof.

14. An immunochromatographic detection method, comprising the steps of:
   1) applying a sample to the membrane of the immunochromatographic detection sensor according to claim 1,
   2) moving the sample along the membrane,
   3) transmitting the probe beam through the optical waveguide, and
   4) determining the intensity of the colored conjugate band by the intensity of the output probe beam, so as to analyze the components of the analyte in the sample.

15. The immunochromatographic detection method according to claim 14, wherein interaction frequency between evanescent waves generated on the surface of the optical waveguide and the colored conjugate in the colored conjugate band is maximized, and thus the absorbance signal from the colored conjugate is greatly amplified to thereby improve the sample detection sensitivity.

16. The immunochromatographic detection method according to claim 14, wherein the wavelength of the probe beam is selected from the group consisting of ultraviolet, visible, and infrared rays.

17. The immunochromatographic detection method according to claim 14, wherein the light source for the probe beam is selected from the group consisting of laser, LED and halogen lamp.

18. The immunochromatographic detection method according to claim 14, wherein the method for transmitting the probe beam through the optical waveguide is performed by using one selected from the group consisting of object lens, prism and diffraction grating.

19. The immunochromatographic detection method according to claim 14, wherein the output probe beam from the optical waveguide is measured using a detector selected from the group consisting of photodiode (PD), photo-multiplier tube (PMT), charge coupled device (CCD), and complementary metal oxide semiconductor (CMOS).

20. The immunochromatographic detection method according to claim 14, wherein the intensity of the output probe beam is measured by any one selected from the group consisting of probe beam intensity at a single wavelength, white light intensity, change in probe beam wavelength, and change in probe beam phase.

* * * * *